(12) United States Patent
Spenser et al.

(10) Patent No.: US 10,231,835 B2
(45) Date of Patent: Mar. 19, 2019

(54) REPLACEMENT HEART VALVE

(71) Applicant: Netanel Benichou, Nir Etzion (IL)

(72) Inventors: Benjamin Spenser, Bat-Shlomo (IL); Netanel Benichou, Nir Etzion (IL)

(73) Assignee: TRUELEAF MEDICAL LTD., Caesaria (IL)

( * ) Notice: Subject to any disclaimer, the term of this patent is extended or adjusted under 35 U.S.C. 154(b) by 0 days.

(21) Appl. No.: 15/311,715

(22) PCT Filed: Mar. 26, 2015

(86) PCT No.: PCT/IL2015/050323
§ 371 (c)(1),
(2) Date: Nov. 16, 2016

(87) PCT Pub. No.: WO2015/173794
PCT Pub. Date: Nov. 19, 2015

(65) Prior Publication Data
US 2017/0095331 A1 Apr. 6, 2017

Related U.S. Application Data

(60) Provisional application No. 61/994,133, filed on May 16, 2014.

(51) Int. Cl.
*A61F 2/24* (2006.01)

(52) U.S. Cl.
CPC .......... *A61F 2/2439* (2013.01); *A61F 2/2412* (2013.01); *A61F 2/2418* (2013.01);
(Continued)

(58) Field of Classification Search
USPC .................................................. 623/1.1–3.1
See application file for complete search history.

(56) References Cited

U.S. PATENT DOCUMENTS 5,716,370 A * 2/1998 Williamson, IV .......................... A61B 17/0469
606/151
2005/0137686 A1 6/2005 Salahieh et al.
(Continued)

*Primary Examiner* — Yashita Sharma
(74) *Attorney, Agent, or Firm* — Robert G. Lev

(57) ABSTRACT

A prosthesic valve for implantation in a body duct that can cover a range of target sizes by a single device. The valve comprises of three main elements:
1) a support cylindrical frame structure that can be collapsed to a small diameter for insertion into the body and that can expand to a large diameter when positioned in the target implantation site, the expansion of the frame being limited by the native valve diameter, which the valve is implanted within. In some cases this may be self-expandable;
2) A frustoconical leaflet support frame that has an inflow side and an outflow side. The inflow side of the leaflet support frame is attached to the cylindrical frame and can be expanded along with the cylindrical frame to a range of diameters up to the diameter of the body duct, while the outflow side is limited in its opening diameter to a smaller constant diameter;
3) Flexible leaflets are attached to the leaflet support frame to create a valve that allows flow from inflow to outflow, but prevents flow in the opposite direction.
A delivery catheter dilates the valve while the frustoconical leaflet support system enables the valve to function (open and close) during the deployment process. Unlike prior prosthetic valves that only allow valve expansion, the valve of the invention may be collapsed if needed in order to re position or retrieve the valve.

15 Claims, 19 Drawing Sheets

(52) U.S. Cl.
CPC .......... *A61F 2/2436* (2013.01); *A61F 2/2433* (2013.01); *A61F 2230/0067* (2013.01); *A61F 2250/0069* (2013.01)

(56) References Cited

U.S. PATENT DOCUMENTS

| | | |
|---|---|---|
| 2011/0040375 A1 | 2/2011 | Letac et al. |
| 2013/0015095 A1 | 1/2013 | Carson et al. |
| 2017/0202665 A1* | 7/2017 | Richter ................. A61F 2/2418 |
| 2017/0296333 A1* | 10/2017 | Iobbi ..................... A61F 2/2418 |

* cited by examiner

REPLACEMENT HEART VALVE

PRIORITY INFORMATION

The present application claims priority as a national stage entry of International Application No: PCT/IL2015/050323, filed on Mar. 26, 2015. The present application also claims priority from U.S. Provisional Patent Application No: 61/994,133, filed on May 16, 2014.

BACKGROUND OF THE INVENTION

The present invention relates to implantable medical devices, particularly, to a percutaneously or minimally invasive heart valve, a delivery system and a method of use.

In recent years, the replacement of diseased or damaged cardiac valves by an artificial valve inserted either percutaneously or by a minimal invasive technique, has become standard for both high risk and non-operable patients. However, both the implantation procedure and the available valve prostheses have some limitations. Such limitations include the fact that hearts in general and diseased heart valves in particular vary widely in size, and finding an optimal valve prosthesis to provide a good fit for a specific diseased valve is a challenging task. Finding an appropriate fit is particularly problematic due to the relatively low accuracy of imaging tools, the large variation in the morphology and tissue properties of diseased valves, and the limited choice of available valve prostheses.

Artificial valves with dimensions providing a non-optimal fit to a specific patient's anatomy may cause clinical complications. For example, implantation of a too small prosthesis may result in paravalvular leak and valve embolization. Implantation of a too large prosthesis for a given diseased valve may cause arrhythmia due to compression on the conduction system, which may cause damage resulting in the patient requiring a pace-maker. In extreme conditions aortic valve replacement using a too large prosthesis can result in aortic annulus rupture.

Currently available prosthetic valves are designed to fit to a native valve having a specific diameter. The cardiac surgeon is required to measure the diseased native valve and to implant a suitably sized prosthetic. However, due to the limitation in measuring and misjudgments, in many cases the valve implanted is not the correct size. If the prosthetic valve is too large and not fully opened, the valve leaflets may include excess material which may result in a shortened life expectancy of the valve. Sometimes an expanded prosthetic valve may stretch the native valve, putting the patient at risk, due to electrophysiological complications and/or aortic root rupture. These complications are very serious and may be dangerous.

Where the prosthetic valve is undersized and is too small for the native valve, it puts the patient at risk of para-valvular leaks, displacement of the implanted valve and over expansion of the prosthetic valve beyond its designed diameter. Such problems may shorten the life expectancy of the valve or compromise its functionality, and puts the patient at risk.

In addition to the inherent problems of valves of the wrong size, the minimally invasive (MIS) implantation procedure as currently practiced has various disadvantages and risks for the patient.

During the implantation, the blood flow is partially or totally blocked by the expanding prosthesis. This requires the surgeons to expedite the prosthesis expansion step which increases the risk of mis-positioning the valve. Sometimes, surgeons use a rapid pacing procedure in order to decrease blood pressure however this may interfere with the accurate positioning of the prosthesis.

These complications increase the stress level of the surgeon and his teams and puts the patient at risk, and the success of the implantation may be compromised.

SUMMARY OF THE INVENTION

Aspects of the present invention are directed to a valve prosthesis that may be accurately fit to a range of native valve diameters.

One embodiment is directed to a valve prosthesis comprising an expandable cylindrical scaffolding having an inlet for installing upstream and an outlet for installing downstream;

a segmented frustoconical inner framework (that serves as a leaflet support structure) having a base attached to the inlet of the cylindrical scaffolding, and an outlet of preset diameter, and a plurality of valve leaflets attached proximally to the inlet side of the inner framework but having distal ends that are free to flex; the outlet of the cylindrical scaffolding being joined to the outlet of the frustoconical inner framework by a flexible membrane, such that the expandable cylindrical scaffolding is expandable to contact the inner wall of a conduit, such that fluid can flow through the segmented frustoconical inner framework from the inlet to the outlet, but reverse flow is prevented by the valve leaflets flexing and coapting together.

Typically, the prosthetic valve is for insertion into a heart, and configured to begin functioning whilst only partially expanded, allowing sufficient blood flow there-through for it to function as a one-way valve during positioning.

Preferably the valve prosthesis is compactable into a small diameter for insertion into the body.

Optionally, the small diameter is up to 6 mm.

Preferably the prosthetic valve may be recompacted for repositioning if required.

Typically, an external surface of the expandable, cylindrical scaffolding is adjustable to be fit into a wide range of native diseased heart valves to maintain optimal resistance to surrounding cardiac wall over the wide range to minimize paravalvular leaks and over-compression of the native valve wall.

Optionally, the valve prosthesis is configured to start functioning prior to full expansion thereby helping to maintain the patient hemodynamics during deployment and facilitating accurate and controlled positioning.

Typically, the expandable, cylindrical scaffolding comprises a self-expandable material.

In some embodiments, the expandable, cylindrical scaffolding comprises a nickel titanium alloy, a chromium cobalt alloy or a stainless steel.

Typically, the leaflet support structure serves as a scaffold for the flexible leaflets.

Optionally, the leaflet support structure has a constant diameter outlet provided by a ring-like element that forces commissures of the valve to be contained within a circle which has a fixed diameter dictated by the ring-like element.

In some embodiments, the leaflet support structure comprises a constant diameter opening limiter made of a wire fabricated from a self-expandable material.

Optionally, the constant diameter opening limiter is fabricated as one piece together with the leaflet support structure.

In some embodiments, the constant diameter opening limiter is configured from three arcs that are each centrally weakened and designed to fold as the valve prosthetic is crimped.

In some embodiments, the leaflet support structure is contoured to mimic a native anatomical line of connection between leaflets and body duct.

In some embodiments, the bottom of the arcs of the leaflet support structure at the inlet side are pivotally attached to the downstream edge of the outer frame to move with the outer frame.

In some embodiments, when the cylindrical outer frame is implanted in a large target site, the cylindrical outer frame presses on the target site to the final deployed diameter and the bottom of the arcs of the leaflet support structure assume a similar diameter as that of the cylindrical outer frame.

In some embodiments, when the expandable stent-like sleeve is implanted in a small target site towards narrow end of range, the bottom of the arcs of the leaflet support structure are constrained to approximately the inner diameter of the outer frame.

Typically, the leaflet support structure comprises three identical closed loops.

Typically, the three identical closed three dimensional rings may be cut from a flat sheet and then shaped to the optimal shape for leaflet support.

Optionally, the three identical closed three dimensional rings are perforated with holes for suturing valve leaflets.

In some embodiments, the leaflet support structure comprises a self-expandable material wire.

Typically, the leaflets are attached to the leaflet support structure and function as a one way valve.

Typically, the leaflets are fabricated from a material selected from the group comprising bovine pericardium, porcine pericardium, equine pericardium, polyurethane, Dacron, nylon and artificial pericardium.

In some embodiments, the leaflets are wrapped along the arc of the leaflet support structure and then sutured through the holes of the arc.

In some embodiments, the leaflet support rings are attached one to the other by suturing at commissures.

Optionally, the leaflet support structure comprises one piece.

Optionally, the leaflet support structure comprises a continuous length of wire.

Alternatively, the leaflet support structure is a single piece sectioned from a tube.

In some embodiments, the outlet of the leaflet support structure is attached to the outer frame by a flexible connecting element.

Optionally, the connecting element comprises a fabric.

In some embodiments, the connecting element comprises PET (Polyethylene trephthalate), tissue, nylon, Dacron, polyethylene or pericardium.

Optionally, a flexible sealing element covers openings between each two adjacent leaflets.

In some embodiments, the sealing element, when flattened is substantially triangular.

In some embodiments the sealing element comprises an implantable grade cloth.

In other embodiments, the sealing element comprises porcine pericardium.

The valve prosthesis may be introduced via a balloon catheter and expanded by inflating the balloon. Additionally or alternatively, the valve prosthetic may be expanded by tensioning a draw string or may be configured to naturally assume an expanded configuration but may be kept compacted by a draw string that is released to allow the prosthesis to expand.

BRIEF DESCRIPTION OF FIGURES

For a better understanding of the invention and to show how it may be carried into effect, reference will now be made, purely by way of example, to the accompanying drawings.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention; the description taken with the drawings making apparent to those skilled in the art how the several forms of the invention may be embodied in practice.

In the accompanying drawings:

FIG. 1a is a schematic cross section view showing the prosthetic valve mounted on a delivery catheter, the approach being through the femoral artery via the aorta for positioning within a defective aortic valve;

FIG. 1b to FIG. 1d are schematic views show three different steps of the deployment of the prosthetic valve, such that FIG. 1b shows the prosthetic valve fully compacted and having its smallest diameter, allowing blood flow around the prosthesis such that the native leaflets prevent back flow by closing against the prosthesis;

FIG. 1c shows a partially opened prosthetic valve with the valve partially functioning by its leaflets opening and closing and with blood flowing both through and around the valve;

FIG. 1d shows the prosthetic valve opened widely such that the native leaflets are tight against the prosthesis preventing blood flow around the prosthesis with the entire flow being through the prosthetic;

FIG. 2a is a cutaway isometric projection of one embodiment of a prosthetic valve of the invention;

FIG. 2b is an exploded view showing the parts of the prosthetic valve in isometric projection prior to assembly;

FIG. 3 shows the expandable, cylindrical scaffolding of the outer frame in accordance with one embodiment;

FIG. 4a is an isometric projection of one embodiment of a frustoconical support structure for the valve leaflets in accordance with one embodiment;

FIG. 4b is an isometric projection of one embodiment of a frustoconical support structure for the valve leaflets in accordance with another embodiment;

FIG. 4c shows the embodiment of FIG. 4a expanded to a large size such that the inlet ends of the support structure for the valve leaflets opens to a diameter that is very much larger than the outlet such that the support structure for the valve leaflets has a clear frustoconical shape;

FIG. 4d shows the embodiment of FIG. 4a expanded to a smaller open size such that the inlet ends of the support structure for the valve leaflets opens to a diameter that is close to that of the outlet such that the support structure for the valve leaflets only tapers slightly and has a shape that is closer to a cylinder;

Figure 5:
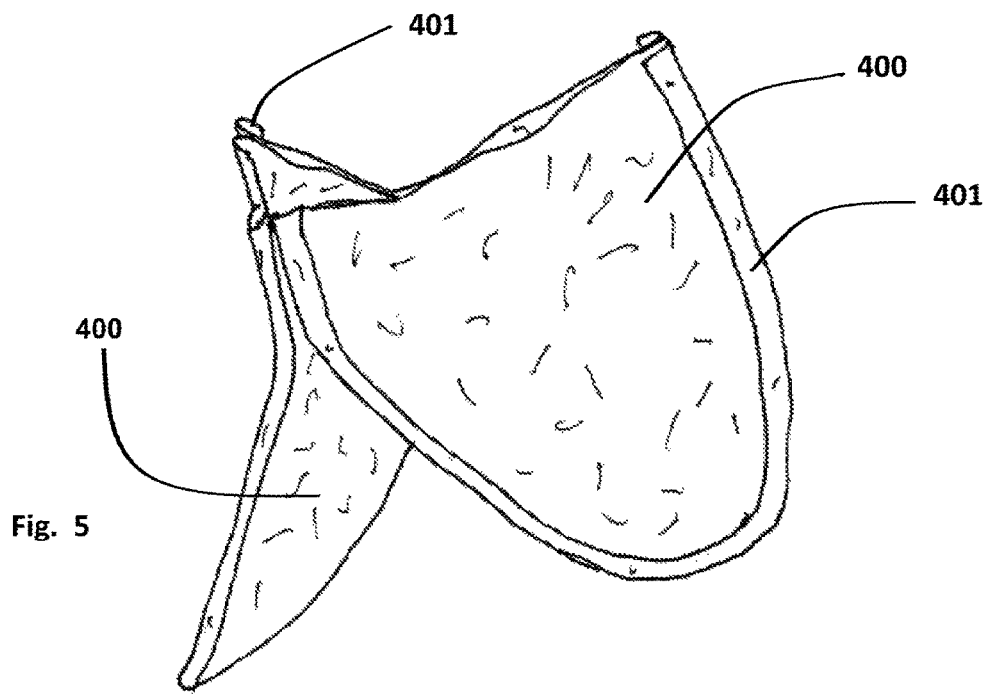
Figure 6:
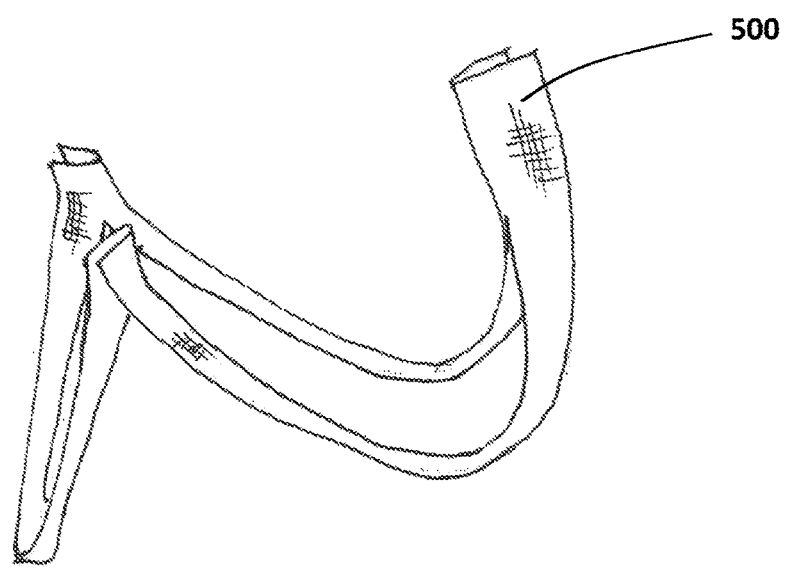
Figure 7:
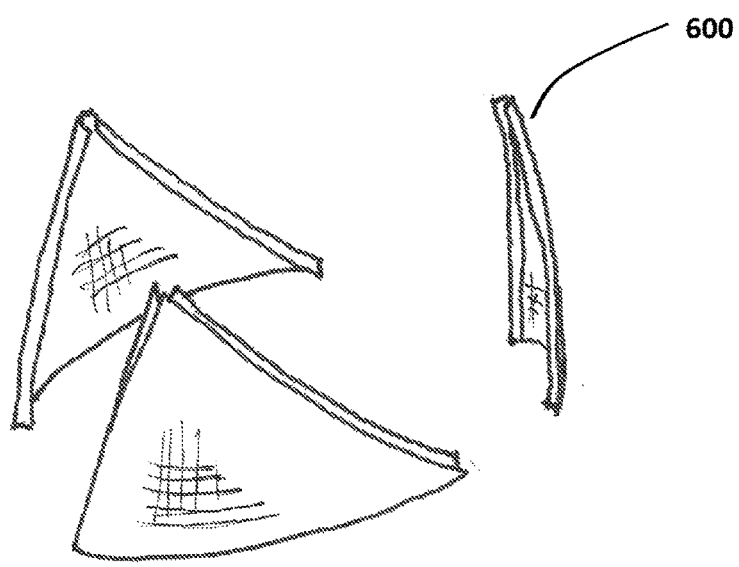
Figure 8A:
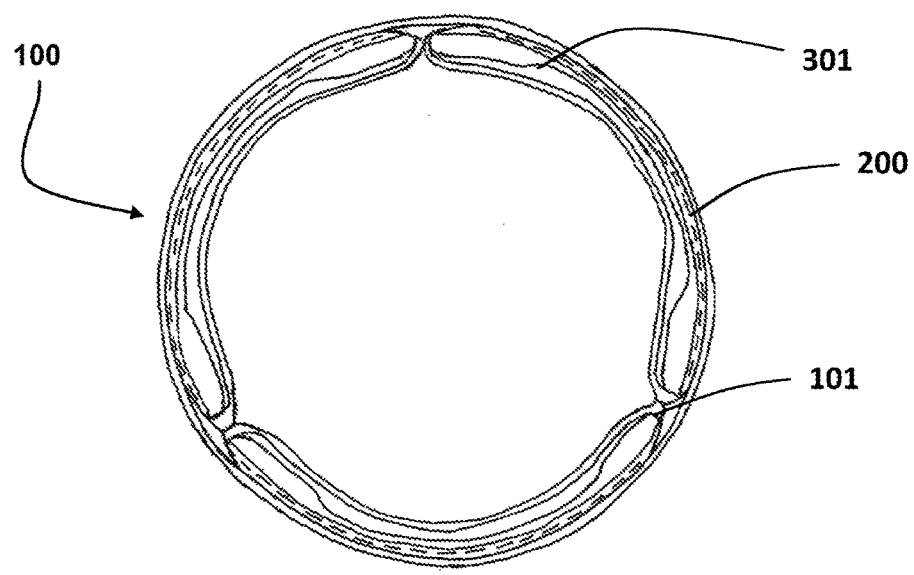
Figure 8B:
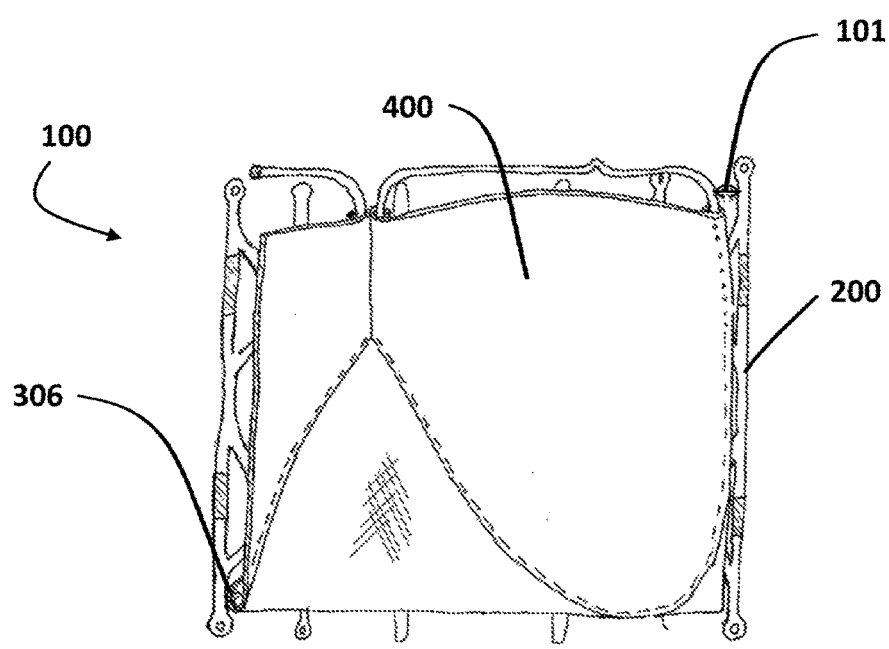
Figure 9A:
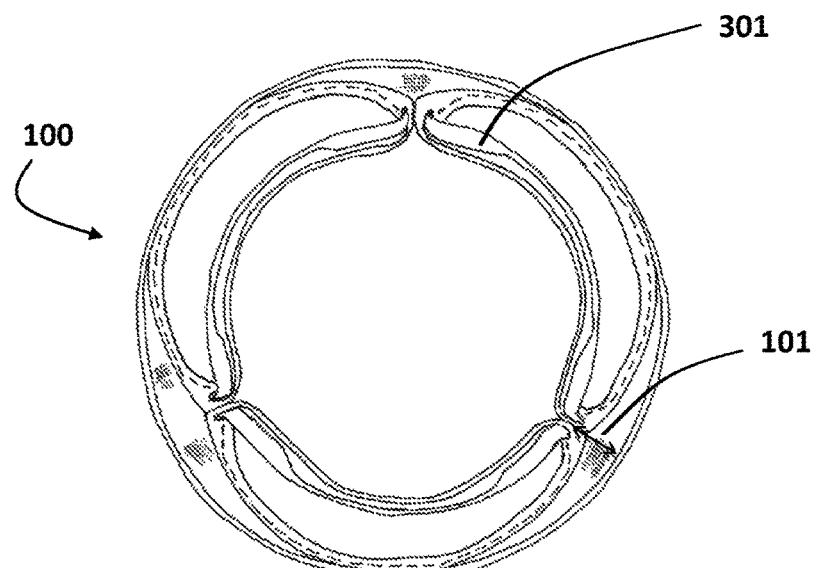
Figure 9B:
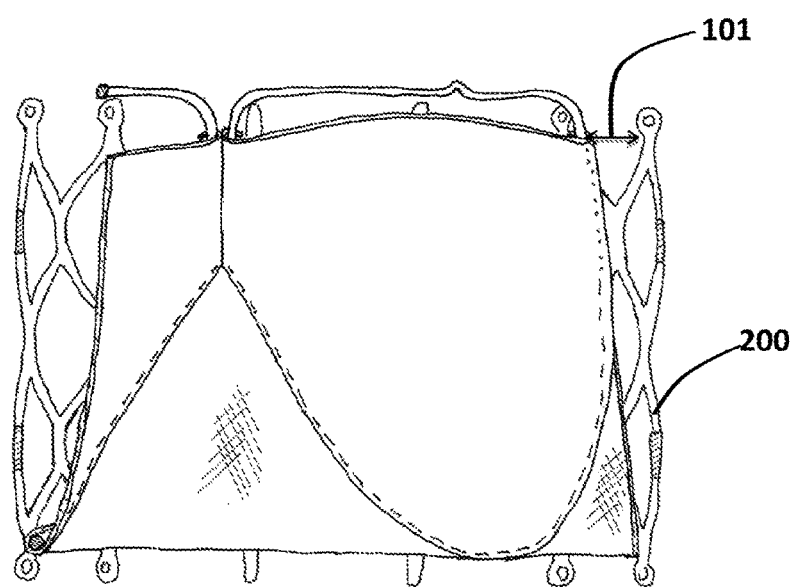
Figure 10A:
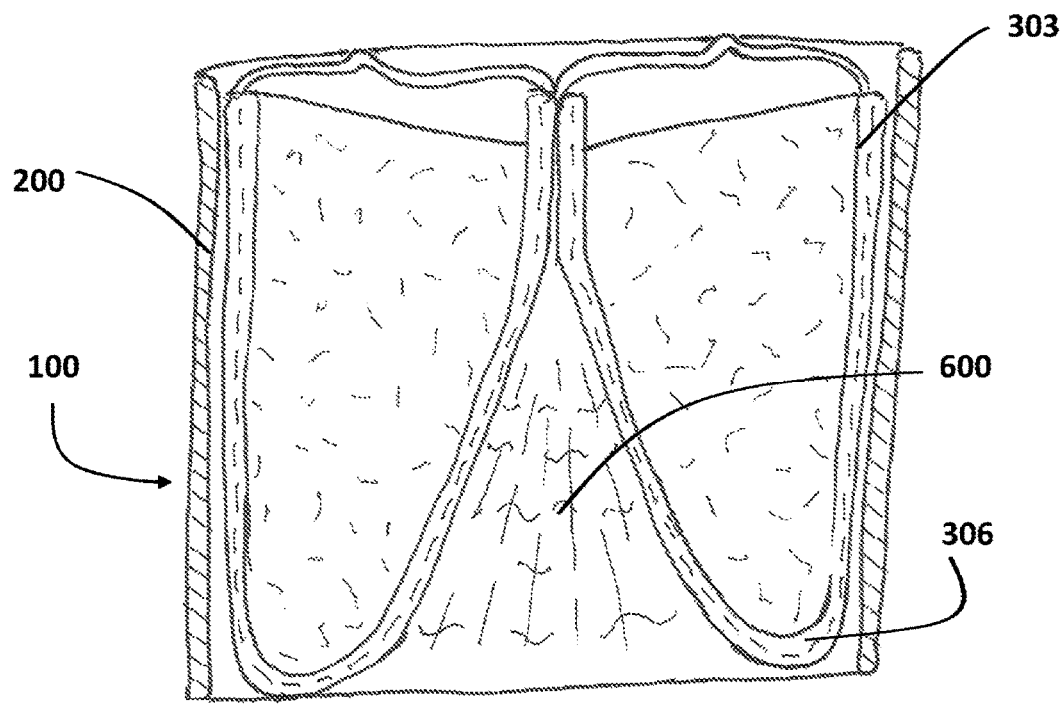
Figure 10B:
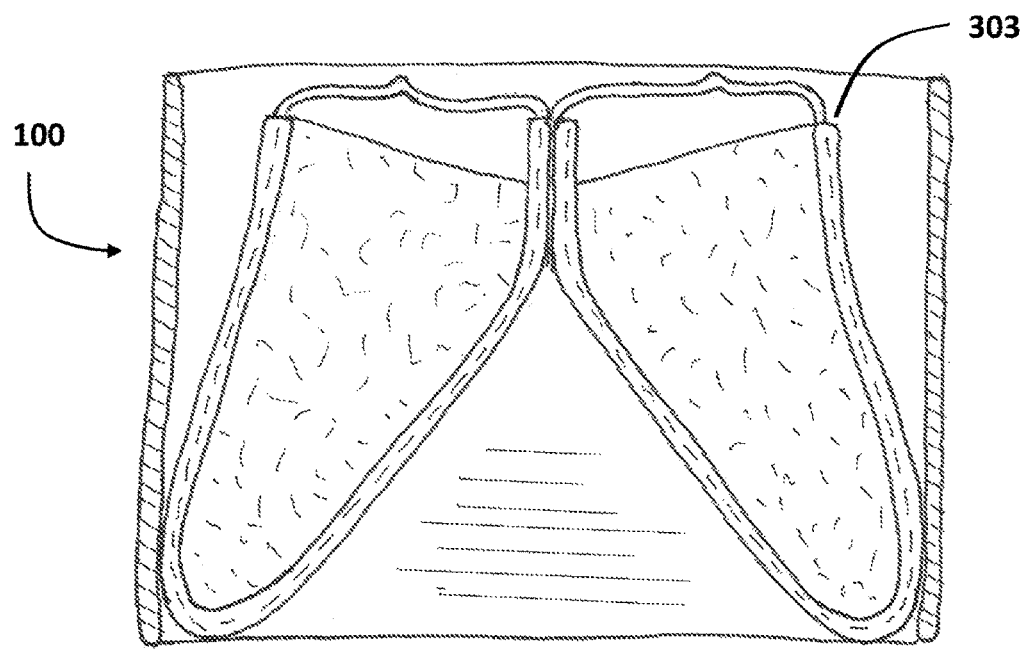
Figure 11:
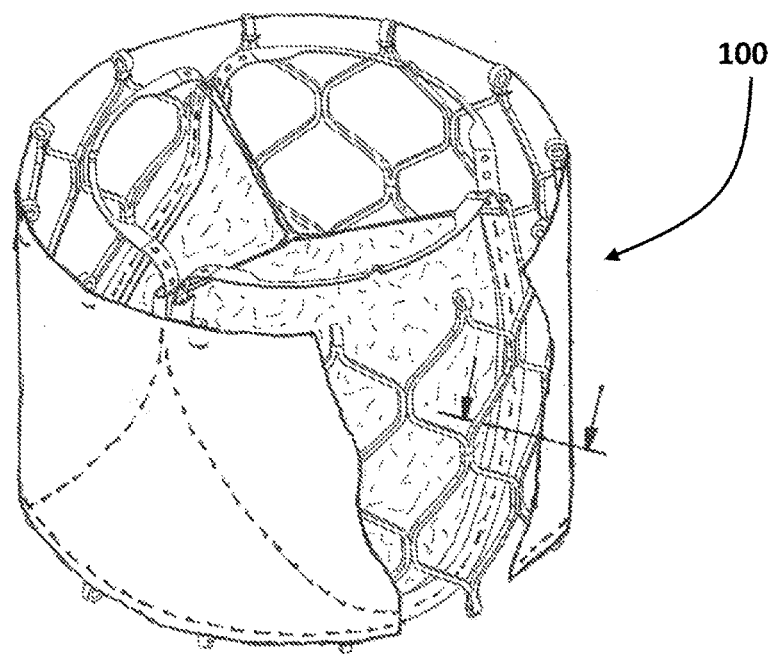
Figure 11:
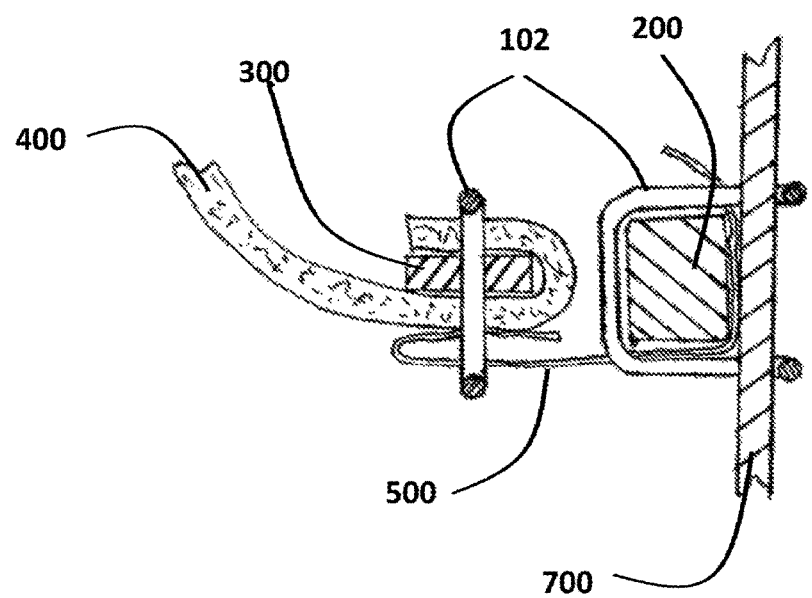
Figure 12:
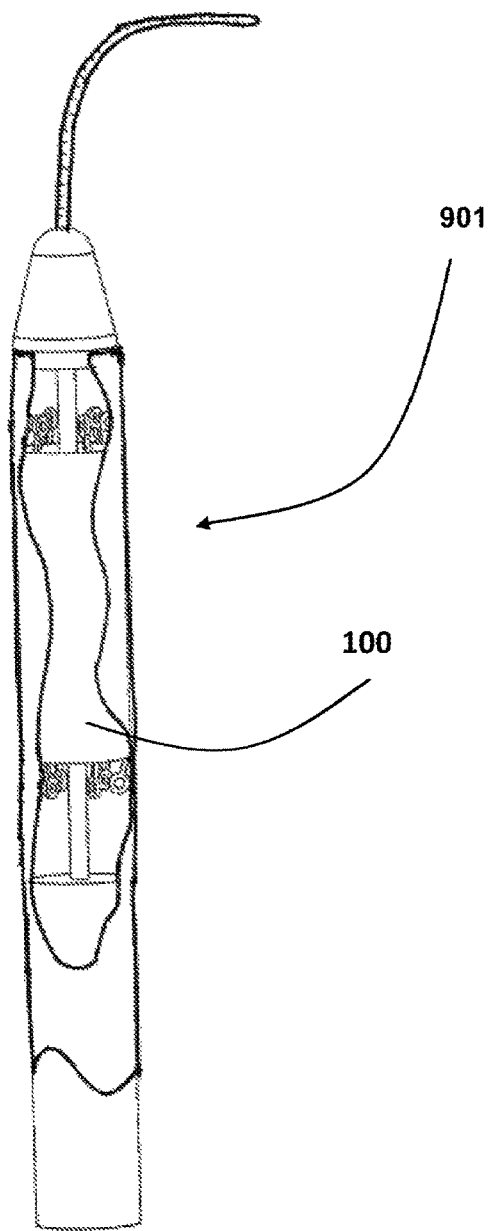

FIG. 5 is a perspective view of the prosthetic valve leaflets;

FIG. 6 is a perspective view of a flexible connecting element, used to connect the leaflets to the cylindrical scaffolding and valve assembly;

FIG. 7 shows a plurality of triangular sealing elements that are part of the valve assembly;

FIGS. 8a and 8b are bird's eye and longitudinal cross section views of an implanted prosthetic configured in a minimum working valve size;

FIGS. 9a and 9b are bird's eye and longitudinal section views of an implanted prosthetic configured in a maximum working valve size;

FIG. 10a is a side view of the valve as fitted within a narrow duct;

FIG. 10b is a side view of the valve as fitted within a wide duct;

FIG. 11 is a view of the prosthetic valve and an enlarged detail thereof, showing how the various elements may be sewn together;

FIG. 12 shows a pre-expanded valve loaded into a sleeve of a delivery catheter.

Figure 13:
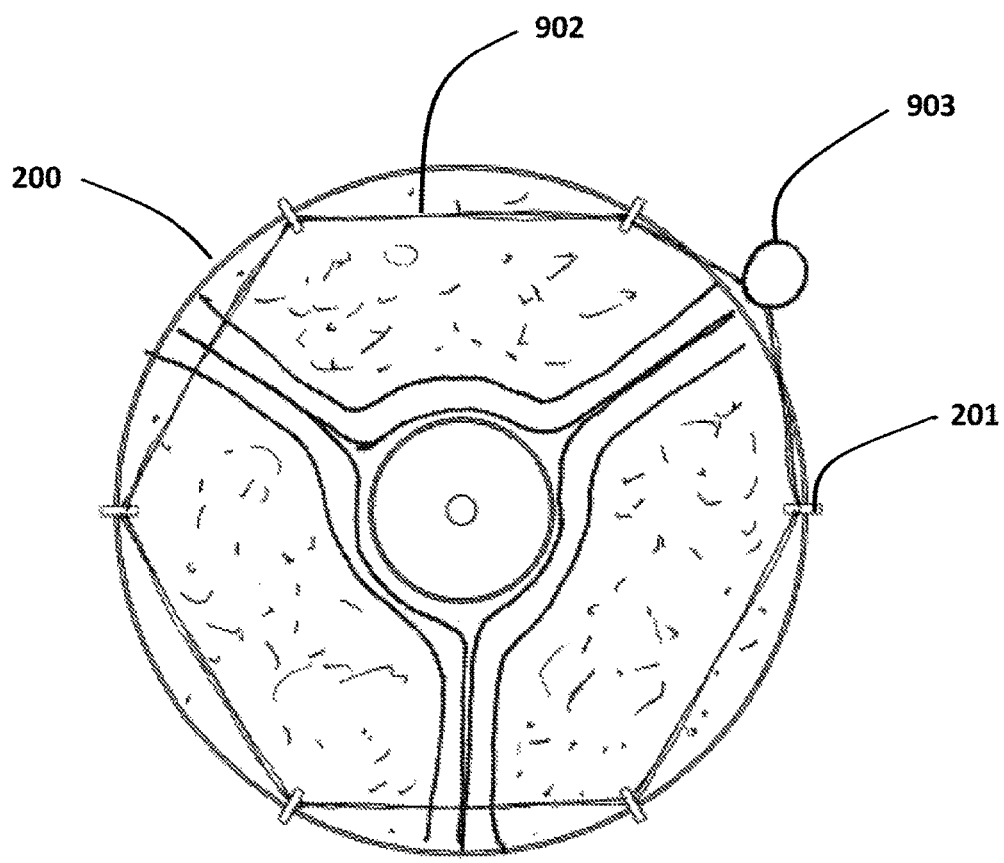

FIG. 13 shows a valve cinching and controlled releasing mechanism that uses a drawstring.

Figure 18A:
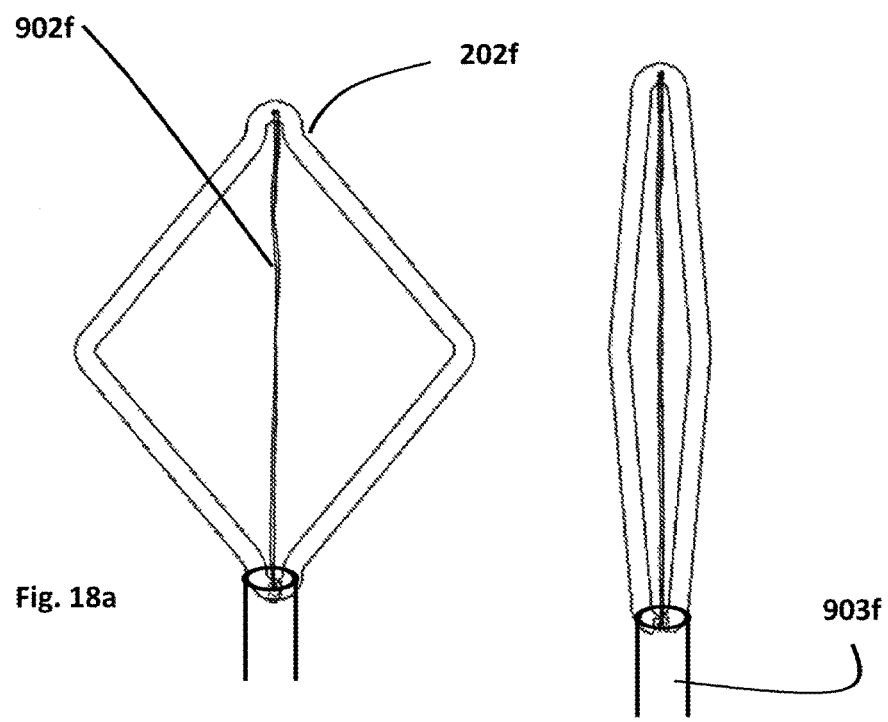
Figure 18B:
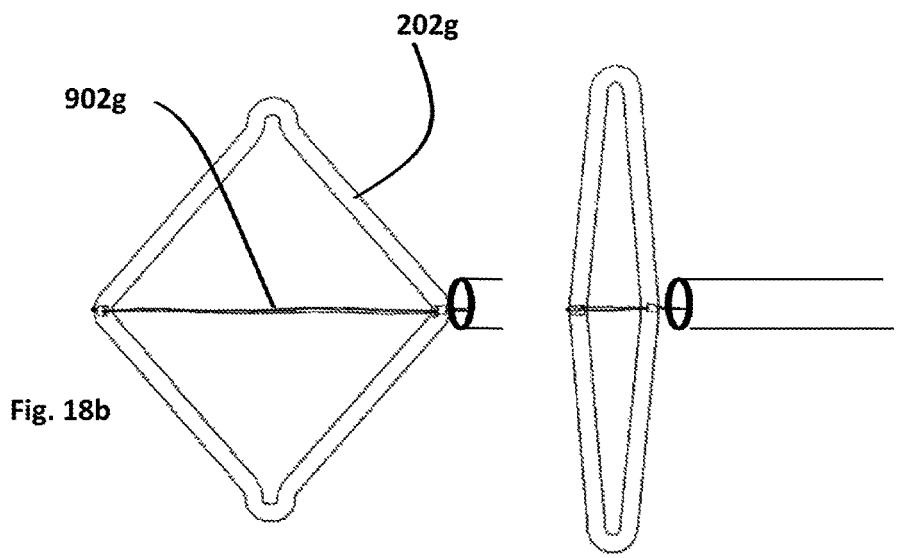

FIGS. 14a-14b, 15a-15b, 16 and 17a-17b show alternative cinching opening closing and releasing mechanisms using drawstrings;

FIG. 18a shows how a normally closed cell may be opened by pulling on a drawstring, and FIG. 18b show how a normally open cell may be closed by pulling on a drawstring.

DETAILED DESCRIPTION

The present invention is directed to a prosthetic valve that has a variable external diameter and may be expanded to fit within body ducts having a range of diameters, particularly within a damaged aortic valve of a heart. In addition to one prosthetic valve being usable in diseased heart valves of different sizes, unlike prior art prosthetic valves the prosthetic valve described herein begins functioning at an early stage of its expansion, allowing sufficient blood flow therethrough for it to function as a one-way valve prior to being fully expanded and deployed. This reduces the requirement for fast positioning and deployment and thus reduces stress on the cardiologist to perform the procedure quickly. In addition, the delivery system of the new valve allows the expanded valve to be compacted to a small diameter and repositioned if required. These features allow the physician greater flexibility during implantation, make the operation less rushed, and increases the surgeon's confidence. Since the valve begins to function early on in the expansion procedure, well before the valve is fully expanded, the danger to the patient from blocking the blood flow are alleviated and rapid pacing procedures are not required. Furthermore, the physician may re compact the valve for repositioning at any time, reducing the stress to the surgeon, which in turn minimizes complications and reduces costs.

The replacement valve consists of an external, cylindrical support frame which can adjust itself to a large range of native diseased valves, in a manner that optimizes resistance from the cardiac wall, minimizing both paravalvular leaks and over-compression of the native valve wall. In addition to the external, cylindrical support frame, the replacement valve further includes an internal construction in the form of a frustoconical leaflet support frame. This leaflet support frame has an outlet with constant diameter for blood flow into the aorta that is only coupled to the external, cylindrical support frame by a flexible membrane such as a fabric, and an inlet that is pivotably attached to the cylindrical support frame at the inlet side. Thus the inlet expands and contracts with the expansion and contraction of the cylindrical support frame and the steepness of the frustoconical leaflet support structure varies with the expanded diameter of the cylindrical support frame.

When installed in a native valve having a relatively small diameter, the cylindrical frame expands to a relatively low diameter and the frusto-conical leaflet support is almost cylindrical, with the variable inlet determined by the cylindrical frame and the fixed diameter outlet having similar diameters. However, if installed in a very wide diameter native valve, the frusto-conical leaflet support is more conical. Generally, however, the replacement valve assumes a conical shape and may be fit to diseased heart valves of different diameters. The device may be available in a narrow range of sizes and, when deployed, the leaflet support structure assumes a frusto-conicalor cylindrical configuration.

Figure 1A:
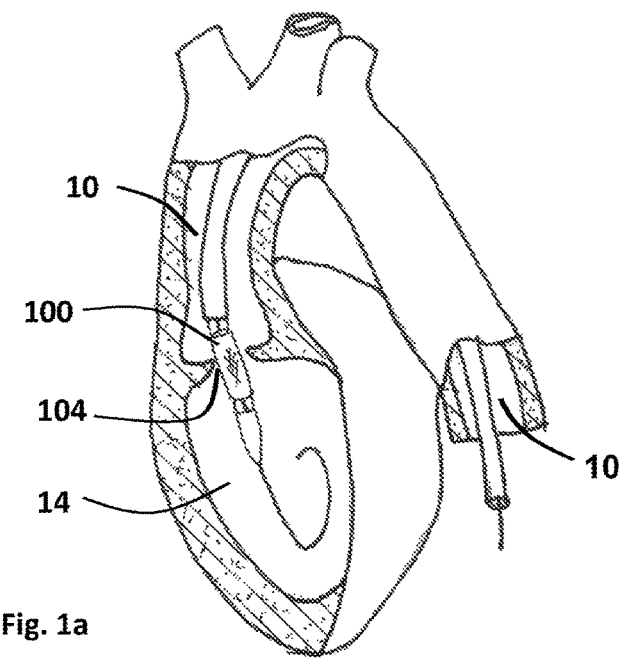

With reference to FIG. 1a a schematic cross section view showing the collapsed prosthetic valve 100 mounted on a delivery catheter 103 is shown, the approach being through the aorta 10 for positioning within a defective aortic valve 104.

Figures 1B, 1C, 1D:
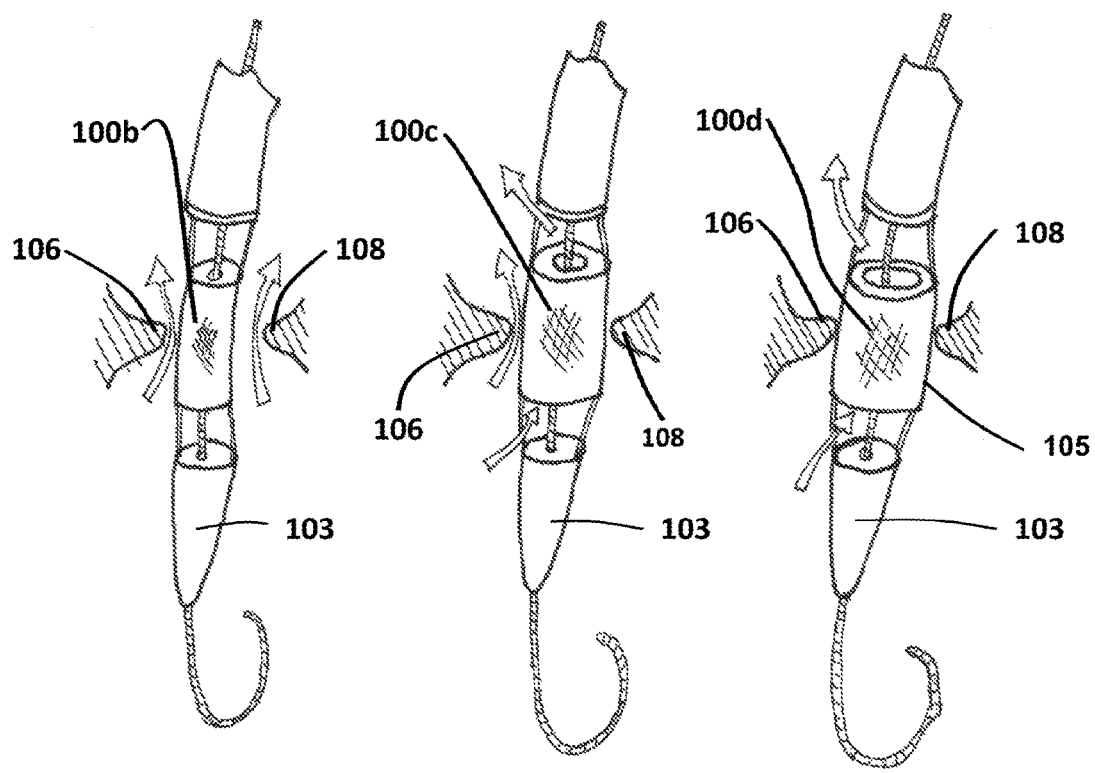

With reference to FIG. 1b to FIG. 1d schematic views of three different steps of the deployment of the prosthetic valve are shown. FIG. 1b shows the prosthetic valve 100b fully compacted on a catheter 103 and having its smallest diameter, allowing blood flow around the prosthetic valve 100b such that the native leaflets 106, 108 prevent back flow by closing against the prosthetic valve 100.

In FIG. 1c the prosthetic valve 100c is partially opened. The walls of the frusto-conical leaflet support structure are approximately parallel to each other and to the external cylindrical frame, nevertheless, the partially opened prosthetic valve functions with its leaflets opening and closing. Blood is pumped from the ventricle 14 to the Aorta 10 both through and around the valve 100c, and the leaflets of the partially opened prosthetic valve 100c prevent blood from flowing back through the prosthetic valve 100c.

In FIG. 1d the prosthetic valve 100d is further opened relative to the prosthetic valve configuration 100c showed in FIG. 1c, the external cylindrical wall 105 of the opened prosthetic valve 100d is wedged tightly against the native valve leaflets 106, 108, thereby preventing blood flow around the prosthesis 100d, so the entire blood flow from ventricle 14 to Aorta 10 is through the prosthetic 100d, and backflow from Aorta 10 to ventricle 14 is prevented by the leaflets of the prosthetic valve 100d as will be discussed in more detail hereinbelow.

In general, the prosthetic valve 100 expands against the native leaflets 106, 108 while maintaining a generally cylindrical shape with its walls 105 remaining parallel.

Figure 2A:
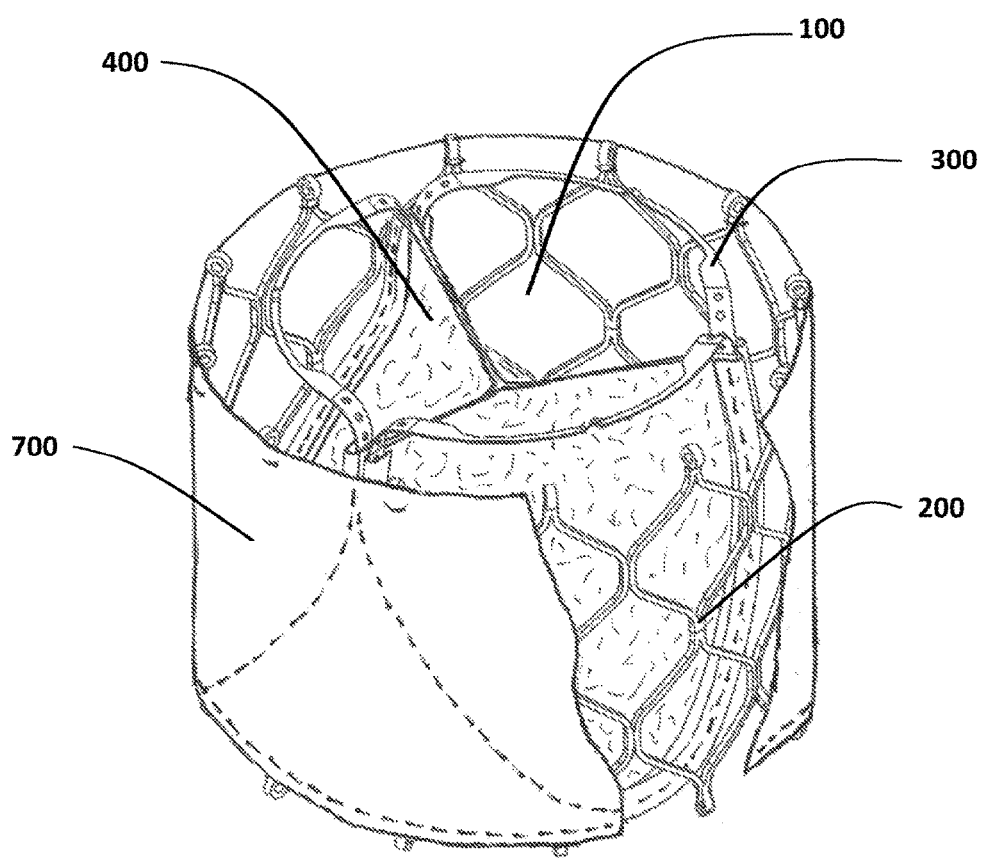
Figure 2B:
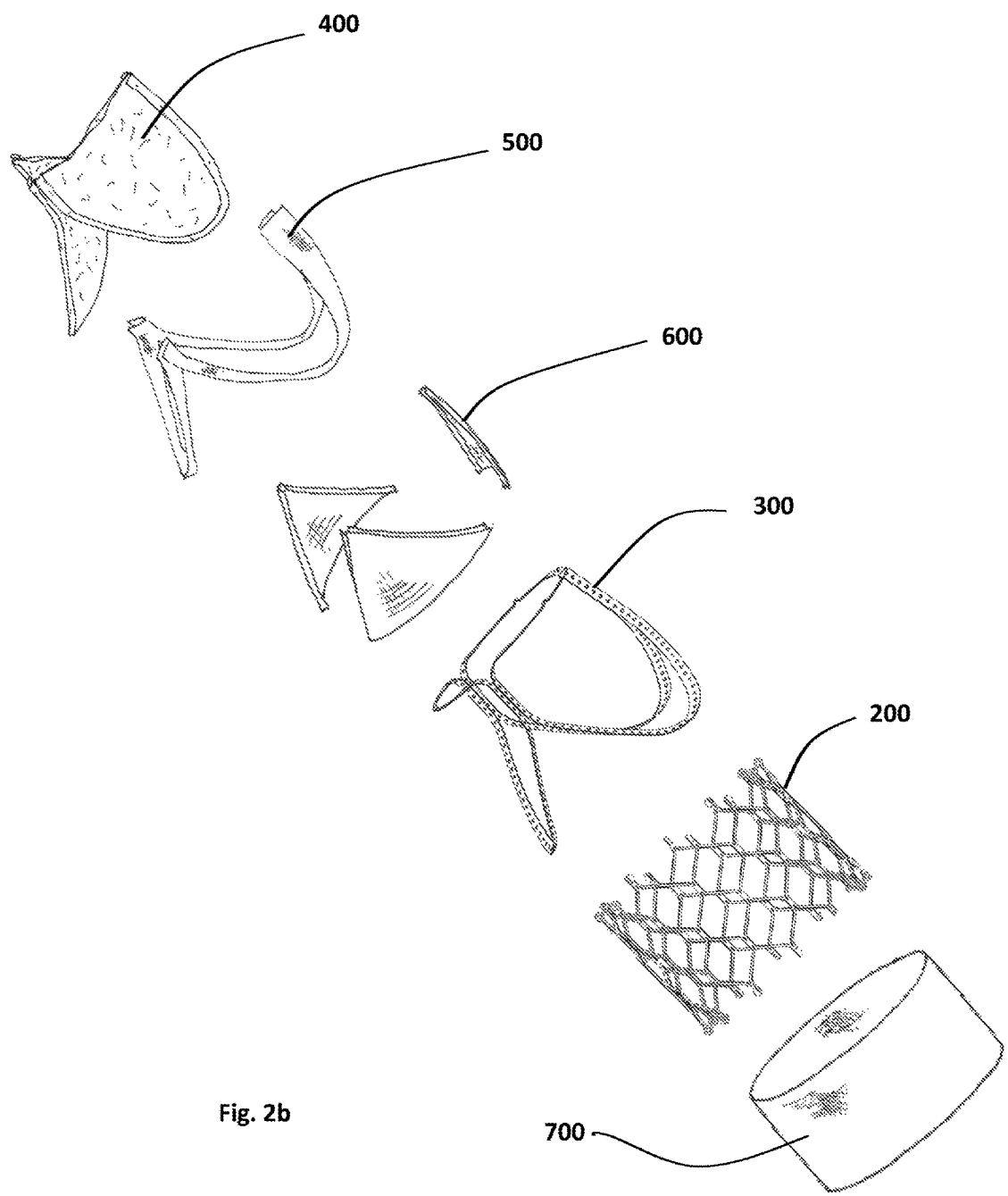

With reference to FIGS. 2a and 2b, one embodiment of the prosthetic valve 100 is shown in more detail. FIG. 2a is a cutaway isometric projection of one embodiment of a prosthetic valve 100, showing the cylindrical frame 200, a frustoconical leaflet support structure 300, leaflets 400 and an outer skirt 700.

FIG. 2b is an exploded view showing the parts of the prosthetic valve 100 prior to assembly. The frame 200, the leaflet support structure 300, the leaflets 400 and the outer skirt 700 are shown separately, as are a flexible connecting element 500 and triangular skirts 600.

Each component is now discussed in more detail and optional structures are provided.

Figure 3:
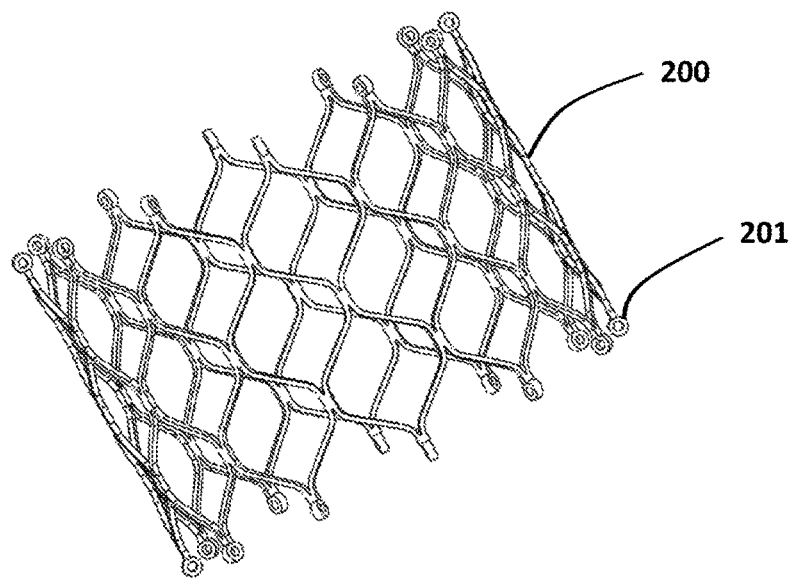

With reference to FIG. 3, the cylindrical outer frame 200 is shown in more detail. Typically, the cylindrical outer frame 200 is fabricated from an expandable material, which may be self-expandable, for example, it may be fabricated from a springy metal, that, once released from a constricting means, self expands until fully expanded, or until further expansion is restricted, such as by the cardiac wall. Alternatively, the cylindrical outer frame 200 may be expanded by a balloon. Balloon expandable stents are well known and so further details are superfluous. It is, however, a feature of some embodiments of the invention that instead of expanding the cylindrical outer frame 200 by pushing from within, a drawstring may be used to pull the outer-frame 200 open. More details of such embodiments are discussed hereinbelow.

The cylindrical outer frame 200 may be crimped to a small diameter for delivery via a catheter 103 (FIG. 1a), for example, and may be dilated to any of a range of final diameters for correctly fitting to the wall of the blood vessel at a target implantation site. Typically, the blood vessel is the cardiac wall at the aortic valve. Cylindrical outer frame 200 may have eyelets 201 through which a wire may be threaded. Where the cylindrical outer frame 200 is self expandable, such as fabricated from a elastic material that tends to expand, or by being fabricated from a shape memory alloy, pulling on the wire collapses the cylindrical outer frame 200 to a small diameter, and gradual releasing the wire allows gradual expansion of the cylindrical outer frame 200. In other embodiments, a wire threaded through eyelets 201 may pull the cylindrical outer frame 200 open.

FIGS. 4a-4d show various embodiments of the leaflet support structure 300.

Figure 4A:
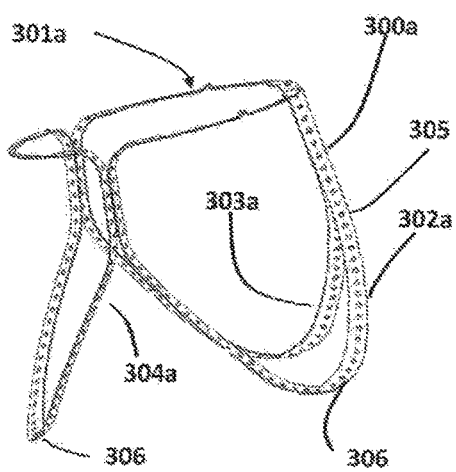
Figure 4B:
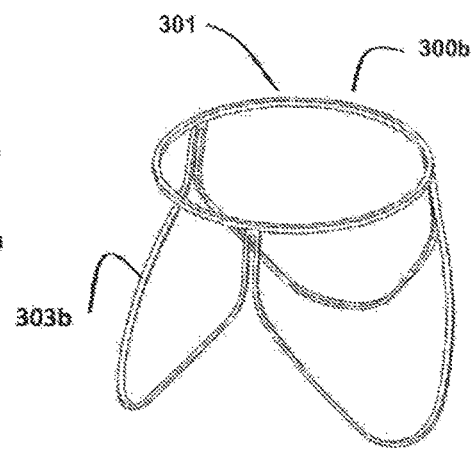

With reference to FIG. 4a, in one embodiment, the leaflet support structure 300a may be assembled from three identical elements 302a, 303a, 304a arranged symmetrically, such that the flat sections thereof are joined to form an outlet 301a that has a fixed diameter. Alternatively, as shown in FIG. 4b, a leaflet support structure 300b, including upper ring 301, and leaflet support elements 303b may be fabricated in one piece, possibly from a length of wire, or cut from a tube, for example.

Figure 4C:
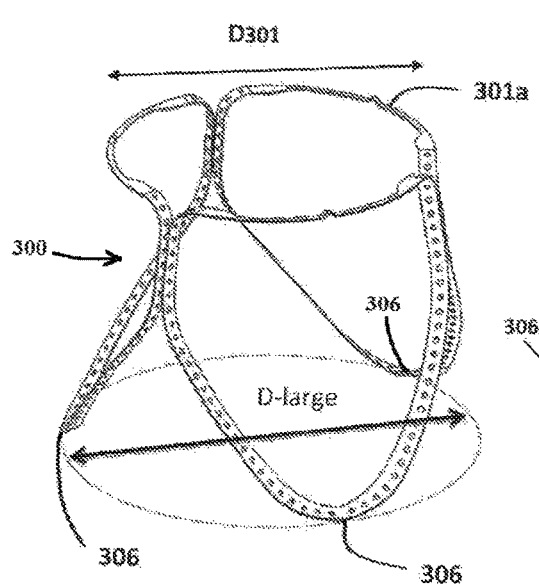
Figure 4D:
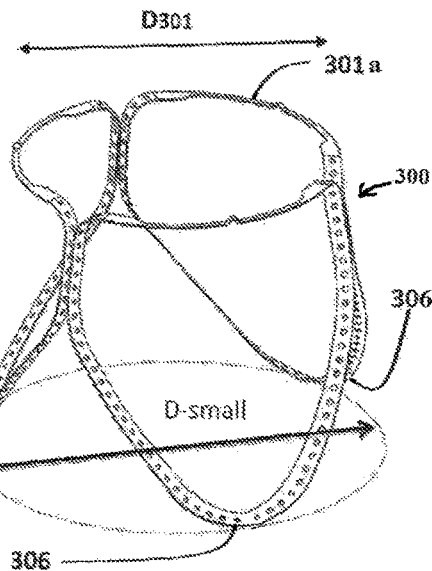

With reference to FIG. 4c, the embodiment of FIG. 4a 300a is shown expanded to a large size such that the inlet ends of the support structure for the valve leaflets opens to a diameter $D_{large}$ that is very much larger than the outlet 301a such that the support structure for the valve leaflets has a clear frustoconical shape;

With reference to FIG. 4d, the embodiment of FIG. 4a 300a is shown expanded to a smaller open size such that the inlet ends of the support structure for the valve leaflets opens to a diameter $D_{small}$ that is close to that of the outlet 301a such that the support structure for the valve leaflets only tapers slightly and has a shape that is closer to a cylinder.

As shown in FIG. 5 Leaflets 400, can be made of bovine, equine or porcine pericardium or from an artificial material, such as polyethylene, nylon or Dacron, for example, are provided. The leaflets 400 are attached to the lower part of the leaflet support structure 300, to the sections 302a, 303a, 304a by outer edge 401 and the upper part of each leaflet is free to flex.

In some embodiments, the attachment is achieved by suturing. Each pair of adjacent leaflets are pressed between two leaflet support structure elements at the commissure area and sutures sew the assembly through the suturing holes 305, with the leaflets being attached along the length of the arch. As shown in FIG. 4a, the leaflet support structure 300a may be fabricated from separate elements 302a, 303a, 304a, or as shown in FIG. 4b, the leaflet support structure 300b may be made in one piece.

Furthermore, the leaflet support structure 300a may be provided with a series of suturing holes 305 around the perimeter of the leaflet supports 302a, 303a, 304a for suturing the leaflets 400 to the leaflet supports 302a, 303a, 304a.

The leaflet support structure 300 has a restricting ring 301 which opens always to a predefined diameter $d_{301}$. This predefined diameter dictates the effective diameter of the outlet of the valve, and thus defines the out flow diameter of the leaflets 400 for the range of deployment diameters of valve 100.

With reference to FIG. 4c and FIG. 4d respectively, the leaflet support structure 300 is frustoconical and the lower points of the leaflet supports 306 may lie on a narrow diameter circle, having a diameter $D_{Small}$ (minimal diameter for example 20 mm), or may lie on a larger diameter circle $D_{large}$ (maximal diameter for example 30 mm). The diameter D of the lower points of the leaflet supports 306 depends on the internal diameter of the cylindrical outer frame 200 to which it is pivotally fastened. When frame 200 is deployed to a small diameter within the possible diameter range, the lower points of the leaflet support structure 306 are pushed radially inward to lie on a narrow diameter circle $D_{small}$. When frame 200 is deployed to a large diameter within the possible diameter range, the lower points of the leaflet support structure 306 assumes the internal diameter of frame 200 $D_{large}$.

The unrestricted, leaflet support structure arcs can be manufactured so that the lower points of leaf support structure 306 lie on a circle having a diameter of anywhere in the range $D_{small}$ to $D_{large}$.

The change in diameter of the circle on which lower points of leaf support structure 306 lie is possible due to the leaf support structure having some elasticity or plasticity. Where the leaflet support structure assumes a non-restricted lower diameter of $D_{large}$, the outer cylindrical frame 200 urges it inward when implanted in a target location which has a diameter smaller than $D_{large}$. In embodiments where the leaflet support structure has a non-restricted diameter of $D_{small}$, the outer cylindrical frame 200 pulls the leaf support structure outward if it is implanted in a target location having a diameter larger than $D_{small}$.

The scaffolding 200 and the leaflet support structure 300 of the prosthetic valve 100 may be fabricated from a balloon expandable material such as Stainless steel 316, or from a self-expandable material such as NiTi—Nitinol (Nickel titanium alloy) which is a shape memory alloy that may be chilled and inserted at below body temperature in a compacted state, so that it expands on returning to body temperature, thereby dilating the prosthetic valve 100. Alternatively, the scaffolding 200 and the leaflet support structure 300 of the prosthetic valve 100 may be opended by pulling on a drawstring as will be described hereinbelow.

In all opening conditions of leaflet support structure 300 the leaflets 400 (FIG. 2) are attached to the leaflet support structure 300 at their lower ends and along the arch, but are free to flex open at their upper ends so that they open and close with changes in blood pressure due to the pumping of the heart wall. The leaflets 400 are supported in an optimal way for proper coaptation to prevent reflow and without excessive leaflet material when the prosthetic valve 100 is opened to a small diameter within the possible diameter range, and without a lack of leaflet material when prosthetic valve 100 is opened to a large diameter within the possible diameter range.

FIG. 5 is a perspective view of the prosthetic valve leaflets 400. The leaflets 400 are shown in their 3D assembly configuration. In one of the possible embodiments, leaflets 400 have folds 401 along the leaflet edges attached to leaflet support structure 300. Folds 401 enable the edges of leaflets 400 to wrap around leaflet support structure 300 resulting in an even stress distribution along the attached edges of the leaflets 400. Where the leaflet support structure 300 is perforated with perforations 305, the leaflets 400 may be sewn to the frustoconical leaflet support structure 300. Otherwise, the edges of the leaflets 400 may be folded around and sewn over the leaflet support structure 300.

With reference to FIG. 6, a flexible connecting element 500 may be used to connect the leaflets 400 and the frustoconical leaflet support structure 300 to the valve assembly 100. In one of the possible embodiments of valve 100 the flexible connecting element 500 connects between the frustoconical leaflet support structure 300 and the cylindrical outer frame 200. In another embodiment, the flexible connecting element 500 connects between leaflet support structure 300 and the outer sleeve 700. Flexible element 500 may be fabricated from a cloth material sheet made of polyethylene terephthalate (PET) or from some other biocompatible flexible sheet such as fixed pericardium, for example. The Flexible element 500 is capable of resisting tension but collapses and folds under compressive forces when frame 200 is crimped to a small diameter of the possible working range of valve 100.

FIG. 7 shows a plurality of triangular sealing elements 600 that may be incorporated in embodiments of the valve assembly 100. The triangular sealing elements 600 fill the gaps between two adjacent leaflets to prevent blood leakage through this area. Triangular sealing elements 600 are typically made of cloth sheet material and are capable of withstanding tension forces, but are generally not capable of withstanding compression forces. They are designed to fold like umbrella fabricate between the spokes of an umbrella as it is collapsed.

The outer skirt 700, the flexible connecting element 500 and the triangular sealing elements 600 prevent blood flow around the leaflets 400, so that all blood flow is through the aperture between the leaflets 400, and, reflow is prevented by coapting of the leaflets together. The outer skirt 700 also facilitates tissue growth to secure the prosthetic in place.

FIG. 8a is a cross-section view of an implanted prosthetic valve 100 configured in a minimum valve size. FIG. 8b shows the prosthetic valve 100 from the side. In FIGS. 8a and 8b, the valve 100 is deployed to the smallest diameter of the possible deployment diameter range, i.e. with the inner leaflet support structure practically cylindrical, having an inlet diameter $d_{small}$ similar to the outlet diameter $d_{301}$. Referring to FIG. 8a, the outlet of the inner frustoconical leaflet support structure 300 is almost the same size as the external cylindrical frame 200, which is opened to a small diameter $D_{small}$ near to the lower end of the possible diameter range, so that the gap 101 between the frustoconical leaflet support structure 300 is almost non-existent, and the frustoconical leaflet support structure 300 is almost the same size as the external cylindrical frame 200 and the bottom of the leaflet support structure 306 shown in FIG. 8b is constrained by the inner diameter of the cylindrical support frame 200. In this position, the frustoconical leaflet support structure 300 is practically cylindrical, yet it nevertheless, suspends the leaflets 400 optimally for proper leaflet coaptation such that the distance between the commissures remains constant due to the constant diameter opening of leaflet support structure ring 301.

In contradistinction, FIGS. 9a and 9b are sectional views of the implanted prosthetic configured in a maximum valve size along the short-axis and longitudinally. FIGS. 9a and 9b show the valve 100 deployed to the maximum diameter of the possible deployment diameter range, at an open leaflets position. Cylindrical outer frame 200 is opened to the largest diameter of the possible diameter range and again, the leaflet support structure restriction ring 301 assumes its constant diameter. In this configuration, the gap 101 between the leaflet support structure restriction ring 301 and the cylindrical outer frame 200 is maximal, whereas the bottom of the leaflet support structure arcs 306 are adjacent to the inner diameter of frame 200, so the leaflet support structure is frustoconical. In this configuration as well, the leaflet support structure 300 suspends the leaflets 400 optimally for proper leaflet coaptation, since the distance between commissures is constant due to the constant diameter opening of leaflet support structure ring 301.

FIGS. 10a and 10b are side views showing the valve 100 in a narrow format as if positioned within a narrow aortic valve 104 and in a wide format, as if positioned in a wider aortic valve. In FIG. 10a the valve 100 is deployed to a small diameter within the possible deployment range and cylindrical frame 200 is constricted to a narrow diameter by the cavity wall. The three commissure areas 303 of the leaflet support structure are in proximity to the cylindrical frame 200, and the bottom of the leaflet support structures 306 are radially positioned on a narrow diameter circle as shown in FIG. 4a by the cylindrical support frame 200. The triangular sealing elements 600 are wrinkled in a manner analogous to the material between the spokes of a collapsed umbrella due to the relatively small gap between adjacent leaflet support structures 301, 302, 303. The leaflets 400 remain optimally supported by the leaflet support structure 300 for proper coaptation.

In FIG. 10b the valve is deployed to a larger diameter within the possible deployment range. Cylindrical frame 200 adjusts itself to the relatively large implantation site diameter, and the three commissure areas of the leaflets 400 slope away from the cylindrical frame 200. The leaflet support structure 300 assumes a wide based frustoconical configuration and the triangular sealing elements 600 are stretched due to the opening of the gap between the adjacent leaflet support structures. The leaflets 400 are again optimally supported by the leaflet support structure 300 and are able to flex and coapt correctly as blood is pumped through the valve.

FIG. 11 shows valve 100 and further shows a detailed cross-section through the attachment of a leaflet 400 to the leaflet support structure 300 and the frame 200, also showing the outer skirt 700. It will be appreciated that this figure is shown for enablement and to provide an understanding of implementation. In this embodiment each leaflet 400 is wrapped around one of the frames 301, 302, 303 of the leaflet support structure 300. The flexible element 500 is attached to the bottom of leaflet 400 and a suture 102 ties the three together. it will be appreciated that there are other ways in which the device may be constructed and the various elements sewn together, so the configuration as shown is by way of example only, and not to be regarded as limiting. In embodiments such as that shown in FIG. 4a, where the leaflet support structure 300 is perforated with suturing holes 304 along its arcs, the suture may be threaded in and out through these holes. In embodiments such as that shown in FIG. 4b, where the leaflet support structure 300 is not perforated with holes, the suture 102 may be wound around the leaflet support structure 300 to hold the leaflets 400, the leaflet support structure 300 and the flexible element 500 together. The flexible element 500 is wrapped around the struts of the cylindrical outer frame 200 and a further suture 103 secures it to the cylindrical outer frame 200 and to the outer sleeve 700.

With reference to FIG. 12, a naturally expanded valve 100a is shown collapsed and loaded into a capsule 901 of a delivery system, which keeps the diameter of the collapsed valve 100 crimped closed. The capsule may have a diameter of about 6 mm, for example.

FIGS. 13 to 18 show different valve cinching and controlled releasing mechanisms that may be used in different embodiments for compacting and expanding the prosthetic valve. Unlike traditional stents and prosthetic valves that are simply released and assume maximum size, by virtue of these cinching and controlled releasing mechanisms, prosthetic valves of the invention may be expanded only partially, nevertheless, the outer frame of 200 of the prosthetic maintains its cylindrical shape as it expands. Furthermore, the expanded prosthetic valve may be reduced in diameter so that its positioning may be adjusted. Indeed, in extreme cases, the expanded prosthetic valve may be cinched closed and withdrawn completely.

Using a drawstring to pull a prosthetic valve 100 open from the outside rather than a balloon catheter to push the valve open from the inside has the advantage that the valve can begin operating when only partially expanded allowing blood to flow therethrough. Using the commonly deployed balloon catheter prevents this as the inflated balloon blocks the passage through the valve. The adjustment feature enabled by using a drawstring instead of a balloon together with the fact that the partially expanded valve has an open outlet and starts to function, allowing blood to pass therethrough, with the leaflets coapting to prevent reflow, reduces a lot of the pressure on the cardiac surgeon, and increases the likelihood of success of the operation.

With reference to FIG. 13, a pull wire 902 is threaded through frame eyelets 201 and the two ends of pull wire 902 are inserted into a cinching tube 903 which is, in the configuration shown, positioned to the side of the prosthetic valve 100. The pull wire 902 and cinching tube 903 extend up to the handle of the delivery system. Pulling on the pull wire 902 while holding the cinching tube 903 in place creates a radial compacting force on the eyelets 201, crimping the cylindrical outer frame 200, which, in this configuration, is naturally open, and thus self expanding. Releasing the tension on the pull wire 902 allows the self-expanding cylindrical outer frame 200 to dilate until it is stopped by the cardiac wall. Since the described mechanism compacts and releases both the inlet and outlet sides of the frame 200 and operate simultaneously, the cylindrical outer frame 200 both crimps and expands while maintaining its cylindrical shape.

FIGS. 14a-14b, 15a-15b, 16 and 17a-17b show alternative cinching, opening, closing and releasing mechanisms.

Figure 14A:
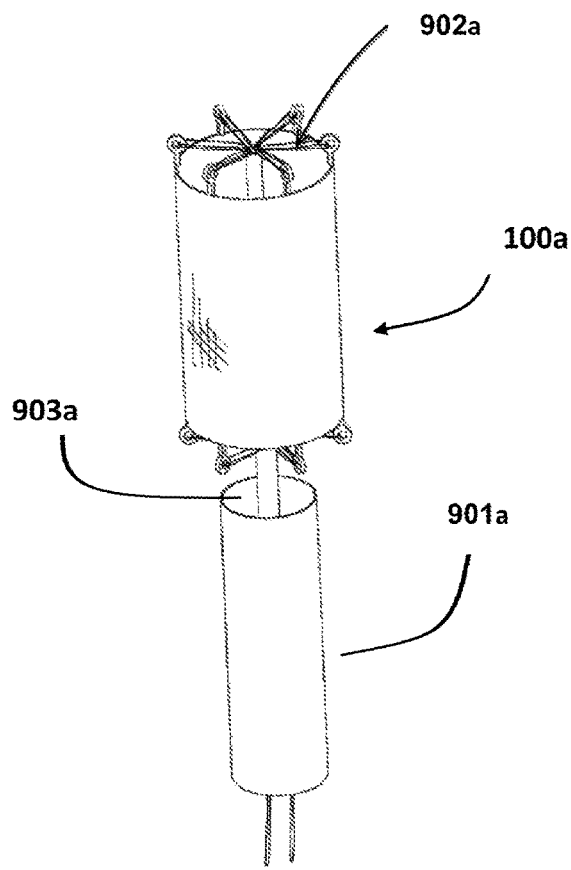
Figure 14B:
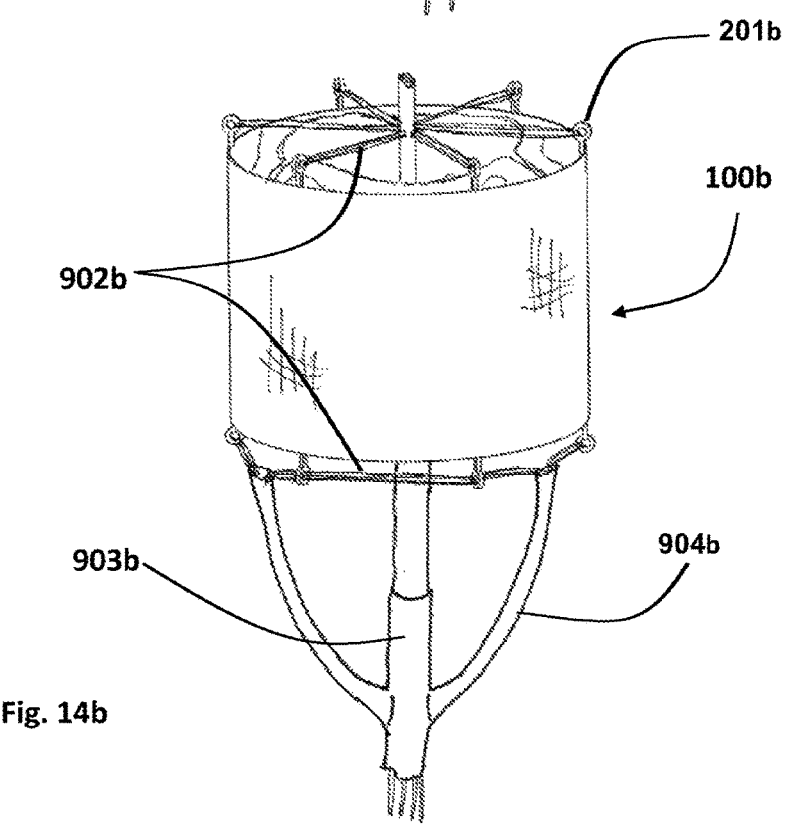

FIG. 14a shows a prosthetic valve 100b just after it has exited the delivery system capsule 901a. The pull wires 902a are in tension and hold the prosthetic valve 100a in a crimped position. In the configuration shown, the cinching tube 903a is located at the center of the valve and pull wires 902a from both side of valve 100a create tension. FIG. 14b shows the valve 100b connected to a delivery system but in its open position. Cinching tube 903b branches out into a three-branched manifold 904b that is trident like. In the embodiment depicted, three loops of wire 902b are threaded through eyelets 201b. Each pair of ends of wires 902b passes through one arm of the trident manifold 904b to the handle of the delivery system 900b. Pulling on wires 902b crimps the self-expanding cylindrical outer frame 200b and releasing the wires 902b, allows the self-expanding cylindrical outer frame 200b to expand. The multiplicity of wires 902b reduces the tension required in each individual wire 902b for crimping the self-expanding cylindrical outer frame 200b. The crimping and expanding mechanism described hereinabove and illustrated in FIGS. 14a and 14b, may be provided on one side of valve 100 such as at the proximal side. It can, however, be implemented on the distal side of valve 100, or on both sides. The manifold support need not be a trident manifold, and may, in other embodiments, have more than three arms.

Furthermore, access to the aortic valve position may be transvascular, via the left ventricle, transapically.

The other (distal) side of valve 100b, depicted in FIG. 14b, shows another possible embodiment of the crimping and expending mechanisms. A few loops (three in this example) are threaded from cinching tube 903b to eyelets 201 around the edge of the cylindrical outer support structure, and back to cinching tube 903b. The wires are simultaneously pulled, crimping the frame 200b, and the release of these wires allows the frame 200b to expand. Furthermore, it will be noted that in all these configurations, the wires only pull and don't push, so any thread used for suturing may be employed.

Figure 15A:
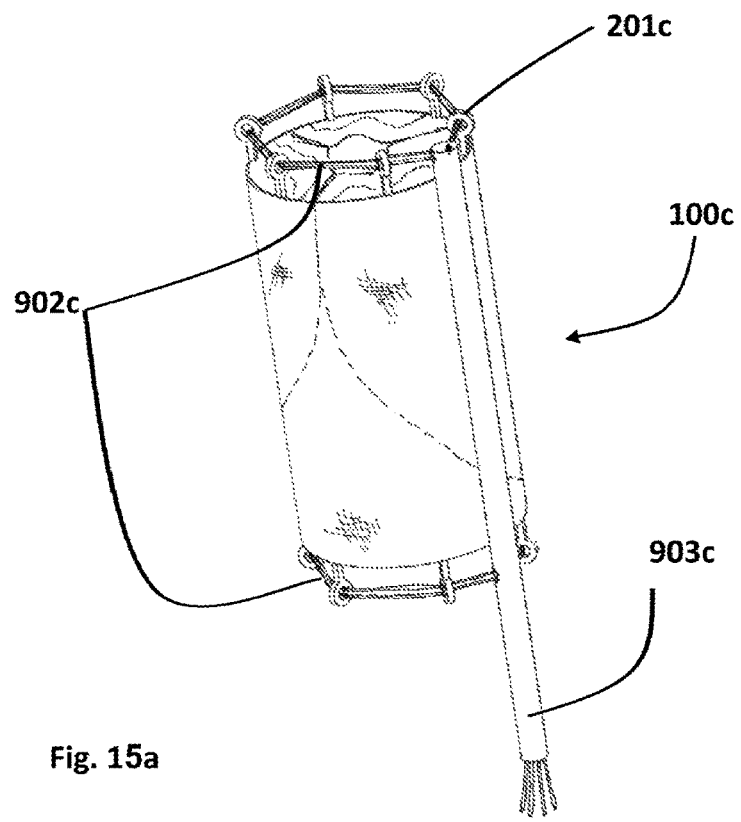
Figure 15B:
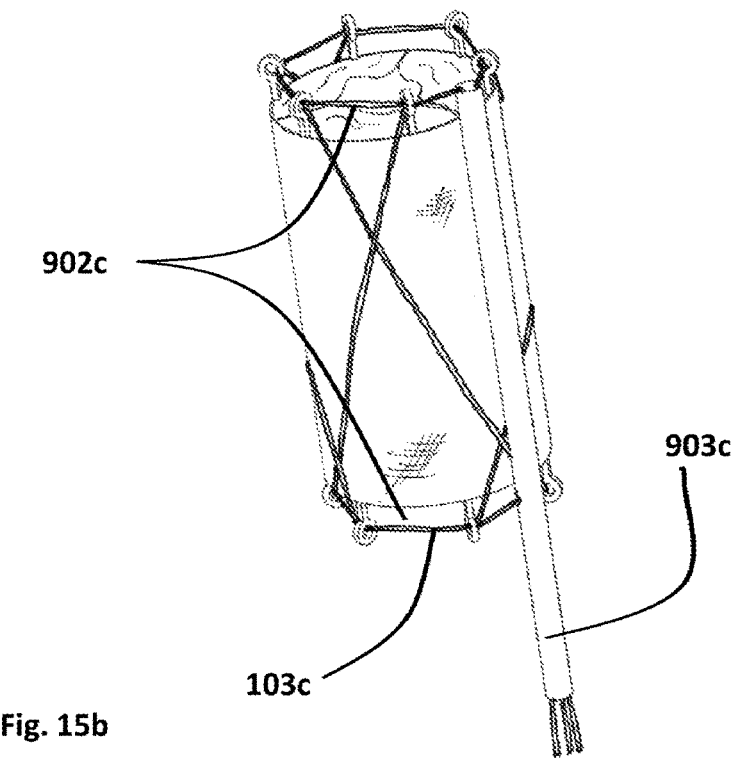

FIG. 15a and FIG. 15b show a similar cinching mechanism to that depicted in FIG. 13 and FIG. 14b at the proximal side. However, cinching tube 903c is placed outside and in parallel to prosthetic valve 100c. The cinching wires 902c create loops through eyelets 201c at both sides of the prosthetic valve 100c. Pulling on the cinching wires 902c crimps the prosthetic valve and releasing them allows the prosthetic valve to expand.

FIG. 15b shows an embodiment that functions in accordance with the same concept as the embodiment depicted in FIG. 15a with one major difference. In the embodiment of FIG. 15b cinching wires 902c extend from one side 103c of prosthetic valve to the other side, criss-crossing from one side to the other. This arrangement allows both the inlet and outlet sides of the valve 100c to be cinched and the tension released gradually such that the cylindrical support structure opens cylindrically. The cinching tube 903c ends at the proximal side 103c of valve 100c. This configuration is not shown in FIG. 15b. In one of the possible embodiments a trident manifold (not shown) can separate from the cinching tube 903c to hold the valve 100c from its proximal side 103c.

Figure 16:
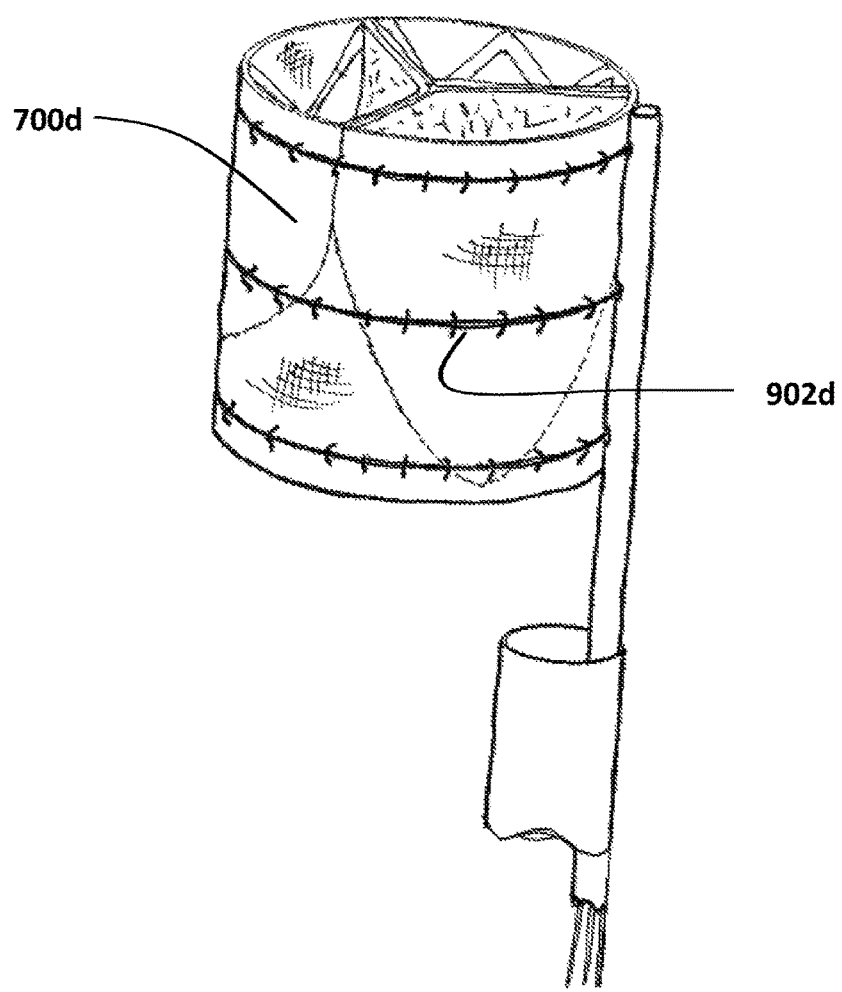

FIG. 16 is yet a further embodiment showing the cinching mechanism depicted in FIG. 13, however, with one major difference. In the embodiment shown in FIG. 16, the cinching wires 902d are looped around the outer sleeve 700d. The wires 902d may be stitched to the sleeve 700d or may penetrate it and be threaded back and forth to help keep the sleeve in its location.

Figure 17A:
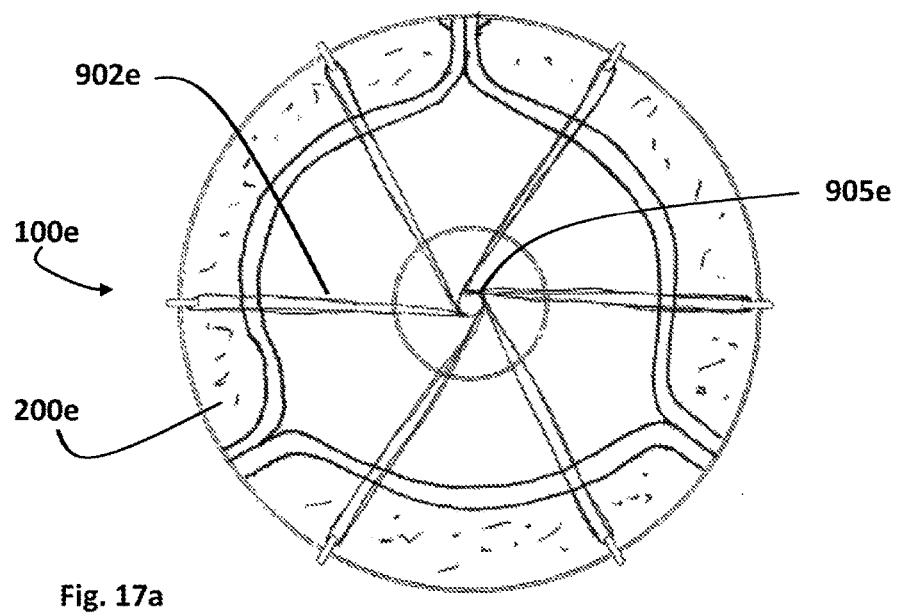
Figure 17B:
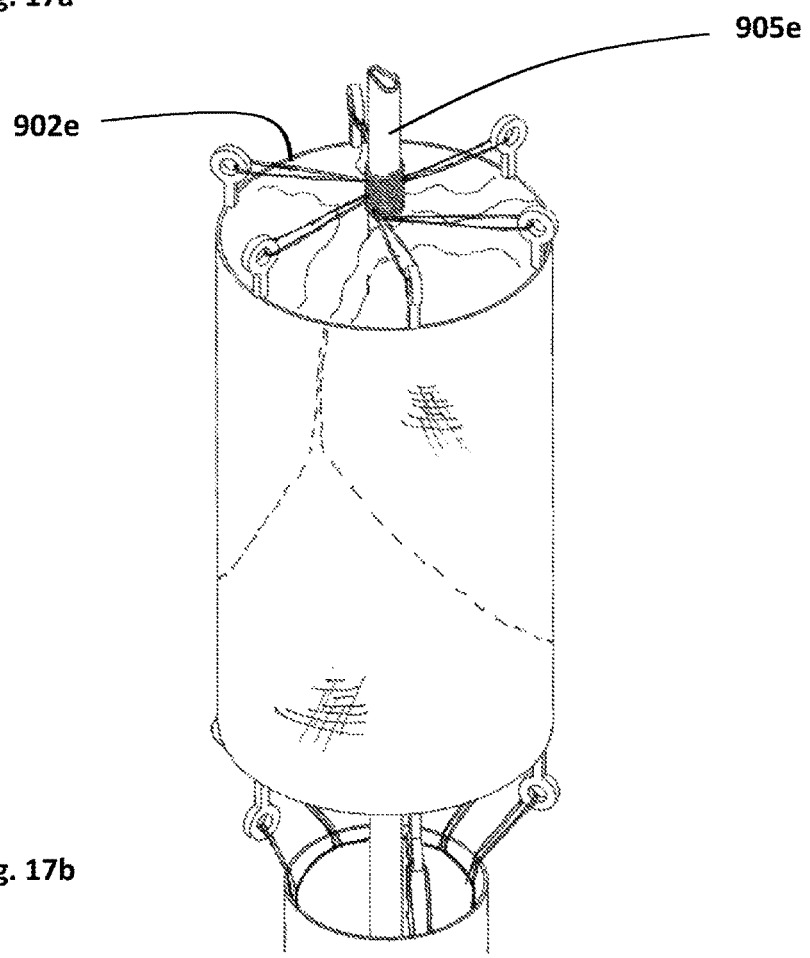

FIG. 17a shows a short axis view of another possible crimping and expanding mechanism. FIG. 17b shows the same crimp mechanism from an isometric view. A torque shaft 905e passes through the center of valve 100e and cinching wires 902e are connected to torque shaft 905e. Rotating the torque shaft 905e coils the cinching wire 902e around it, force it to shorten and thus crimp the valve 100e. Rotating the torque shaft 905e in the opposite direction releases cinching wires 902e and thus frame 200e expands.

FIGS. 18a and 18b schematically show a further cinching mechanism. The mechanism is depicted for one cell of the multiple of cells comprising a frame. FIG. 18a depicts a self-expandable cell 202f which is shaped to assume a normally closed position. The two figures of FIG. 18a present a cell in its closed (right) and open (left) positions. The cinching wire 902f is fixed to the upper apex of cell 202f and is threaded through a hole in the bottom apex of cell 202f and then inserted into cinching tube 903f. Pulling on cinching wire 902f while holding cinching tube 903f, foreshorten the distance between the upper cell 202f apex and the bottom cell 202f apex. In case frame 200f longitudinal axis is vertical the said action expands frame 200f.

Reference is now made to the left figure of FIG. 18b. Here cell 202g is shaped to assume a normally open position. Pulling on cinching wire 902g, while holding cinching tube 903g causes the left and right apexes to get closer. Assuming frame 200 longitudinal axis is vertical, this action crimps frame 200. The operating directions could be switched by switching the unloaded preset of cell 202g.

Where a balloon catheter is used to expand the prosthetic valve, the expansion is by pushing from within. This tends to flatten the frustonical inner part 300 into a cylindrical shape adjacent to the surrounding outer scaffolding 200. An advantage of having a crimped prosthetic valve that is expanded by pulling on a drawstring or one that is naturally expanded and is held crimped by a drawstring that is then released, rather than using a balloon catheter to push the prosthetic open, is that this enables the outer scaffolding 200 to expand cylindrically whilst the inner part to which the leaflets are attached may remain frustroconical, since the expanding is by pulling from the outside rather than pushing from the inside.

The present invention is thus directed to providing a prosthetic valve which can be expanded to a range of diameters for optimally fitting a wide range of diseased heart valves. As described, the prosthetic valve has three leaflets and is typically used as a replacement aortic valve. It will be appreciated, however, that it could be used as a replacement mitrial valve, or positioned within the aorta and not within the heart. The figures and description relate to its use in a human, but it could be applied to other mammals. Indeed, it could be used as a replacement valve in a three chambered heart such as in an amphibian or reptile (not crocodile), for example.

The valve structure consists of an outer cylindrical section that is typically an expandable stent-like structure and an inner leaflet support structure which supports the valve moveable leaflets and which is frustoconical. The inlet ends of the outer cylindrical section and the leaflet support structure are coupled together by sutures or links. Leaflets made of pericardium, typically bovine, equine or sheep pericardium, or from Dacron, nylon or polyethylene is attached to the leaflet support structure. Triangular pieces of pericardium, Dacron, nylon or polyethylene is positioned in the spaces between the leaflets and folds like the material between spokes of an umbrella, allowing the frustoconical inner leaflet support structure to be expanded to frustoconical shapes of different base sizes. The outlet of the frustoconical inner leaflet support structure is set to a fixed diameter. Consequently, regardless of how widely the prosthetic is expanded over a large predefined range, the three leaflets coapt correctly preventing regurgitation. The prothetic valve assembly may be crimped to a small diameter of about 6 mm for introduction into the blood system via a small diameter blood vessel and expanded to larger diameters, with a maximum pre-configured diameter that is typically about 30 mm.

The opening of the inner structure provides an outlet of the valve that is constrained to a diameter which represents the lower range of a normal human aortic valve, for example about 20 mm. However, the inlet of the same valve can expand to larger diameters in the upper range of human aortic valves in diseased hearts.

The described valve will typically be fit to human native diseased valves having diameters in the range of 20 to 30 mm.

If the valve prosthetic is implanted within a 20 mm native valve, the inlet and outlets of the prosthetic valve are opened to around 20 mm. The outlet is constrained by the constraining element of the valve structure while the inlet is constrained by the patient's aortic natural valve anatomy. If, however, the valve is implanted in, say, a 30 mm native valve, the outlet of the prosthetic valve again opens to around 20 mm. Again the outlet is constrained by the constraining element of the valve. The inlet of the prosthetic valve opens to around 30 mm which is the fully open diameter in this example, and coapts with the patient's aortic natural valve wall. The final geometry of the leaflet support structure is frusto-conical with an inlet of around 30 mm and an outlet of around 20 mm. Regardless of the shape assumed by the leaflet support structure, the expandable stent-like outer structure opens to a generally cylindrical shape while adapting to the shape of the patient native aortic valve.

The expandable stent-like structure of the prosthetic valve is connected to the leaflet support structure near the inlet. In some embodiments, the inlet of both the leaflet support structure and of the expandable stent-like structure have the same diameter, while the outlet side will allow different diameters of the inner leaflet support structure and the outer expandable stent-like structure parts. The connection between the inner leaflet support structure and the outer expandable stent-like structure functions as a hinge, allowing a range of angles between the two parts, determined by the preset outlet diameter of the inner leaflet support structure and the final diameter of the outer structure, which is determined by the anatomy of the patient.

The inner leaflet support structure and the outer expandable stent-like structure may be connected by a continuous flexible membrane or fabric, such as Dacron, nylon or polyethylene or sections of pericardium which fold like the fabric of in a manner analogous to a collapsed umbrella thereby allowing different diameters of the inner leaflet support structure and the outer expandable stent-like structure.

The valve structure described above allows the leaflet coaptation line to work in an optimal manner, since the length of the coapting surfaces does not depend on the patient anatomy.

The scope of the present invention is defined by the appended claims and includes both combinations and sub combinations of the various features described hereinabove as well as variations and modifications thereof, which would occur to persons skilled in the art upon reading the foregoing description.

In the claims, the word "comprise", and variations thereof such as "comprises", "comprising" and the like indicate that the components listed are included, but not generally to the exclusion of other components.

The invention claimed is:

1. A valve prosthesis for installation in a body duct comprising: an expandable, cylindrical outer scaffolding having an inlet for installing upstream and an outlet for installing downstream; a segmented frustoconical inner framework having a base attached to the inlet of the cylindrical scaffolding, and an outlet of preset diameter provided by a ring-like element that forces commissures of the valve prosthetic to be contained within a circle which has a fixed diameter dictated by the ring-like element; a plurality of prosthetic valve leaflets attached proximally to the inlet side of the inner framework but having distal ends that are free to open and close; the outlet of the cylindrical scaffolding being joined to the outlet of the frustoconical inner framework by a flexible membrane, such that the expandable cylindrical outer scaffolding is expandable to contact an inner wall of the duct, allowing fluid flow through the segmented frustoconical inner framework from the inlet to the outlet, but preventing reverse flow by the valve leaflets flexing and coapting together;

wherein the ring-like element serves as a leaflet support structure and comprises a wire fabricated from a self-expandable material or the ring-like element is fabricated as one piece together with a leaflet support structure comprising three arcuate elements which are pivotally attached to the downstream edge of the expandable, cylindrical scaffolding to move with the expandable, cylindrical scaffolding to fold as the valve prosthetic is crimped.

2. The valve prosthesis of claim 1 for insertion into a heart, and configured to begin functioning whilst only partially expanded, allowing sufficient blood flow therethrough for it to function as a one-way valve during positioning.

3. The valve prosthesis of claim 1 being compactable for insertion into the body duct.

4. The prosthetic valve of claim 1 wherein an external surface of the expandable, cylindrical scaffolding is adjustable to fit a wide range of native diseased hearts by maintaining optimal resistance to surrounding heart wall over a wide range, thereby minimizing both paravalvular leaks and over-compression of the surrounding heart wall.

5. The valve prosthesis of claim 1, wherein at least one of the expandable, cylindrical outer scaffolding and the frustoconical inner framework comprises a self-expandable material selected from the group consisting of nickel titanium alloy, chromium cobalt alloy and stainless steel.

6. The valve prosthesis of claim 1 wherein the leaflet support structure is contoured to mimic a native anatomical line of connection between the valve leaflets and the body duct.

7. The valve prosthesis of claim 6 wherein when the expandable, cylindrical scaffolding is implanted in a large target site towards wider end of range, the expandable, cylindrical scaffolding presses on the target site to the final deployed diameter and the bottom of the arcuate elements of the leaflet support structure assume a similar diameter as that of expandable, cylindrical scaffolding and when implanted in a small target site towards narrow end of range, the bottom of the arcuate elements of the leaflet support structure are constrained to approximately an inner diameter of the expandable, cylindrical scaffolding.

8. The valve prosthesis of claim 6 wherein the leaflet support structure comprises three closed loops.

9. The valve prosthesis of claim 6 wherein the prosthetic leaflets are fabricated from a material selected from the group including bovine pericardium, porcine pericardium, equine pericardium, polyurethane, Dacron, nylon and artificial pericardium.

10. The valve prosthesis of claim 1 wherein at least one of the following limitations is true: the prosthetic leaflets are wrapped along the arc of the leaflet support structure and then sutured to the arcuate elements, and the arcuate elements are attached one to each other by suturing at commissures.

11. The valve prosthesis of claim 1 wherein a flexible sealing element covers openings between each two adjacent leaflets.

12. The valve prosthesis of claim 11 wherein the sealing element, when flattened is substantially triangular.

13. The valve prosthesis of claim 11 wherein the sealing element comprises an implantable grade cloth.

14. The valve prosthesis of claim 11 wherein the sealing element comprises porcine pericardium.

15. The valve prosthesis of claim 1 provided in a cinched configuration with at least one drawstring for expansion by tensioning the draw string.

* * * * *